United States Patent
Fujiwara et al.

(10) Patent No.: US 9,886,755 B2
(45) Date of Patent: Feb. 6, 2018

(54) IMAGE PROCESSING DEVICE, IMAGING SYSTEM, AND IMAGE PROCESSING PROGRAM

(71) Applicant: KONICA MINOLTA, INC., Tokyo (JP)

(72) Inventors: Koichi Fujiwara, Osaka (JP); Osamu Toyama, Kakogawa (JP); Hiroshi Yamato, Amagasaki (JP); Kenta Shimamura, Tatatsuki (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 14/631,300

(22) Filed: Feb. 25, 2015

(65) Prior Publication Data
US 2015/0254841 A1 Sep. 10, 2015

(30) Foreign Application Priority Data

Mar. 7, 2014 (JP) .................................. 2014-045084

(51) Int. Cl.
*G06K 9/00* (2006.01)
*G06T 7/00* (2017.01)
(Continued)

(52) U.S. Cl.
CPC .............. *G06T 7/0012* (2013.01); *A61B 5/08* (2013.01); *A61B 6/5205* (2013.01); *A61B 6/5217* (2013.01); *A61B 6/5264* (2013.01); *G06T 5/003* (2013.01); *G06T 7/0016* (2013.01); *G06T 7/20* (2013.01); *G06T 7/251* (2017.01); *G06T 7/254* (2017.01); *A61B 6/486* (2013.01);
(Continued)

(58) Field of Classification Search
CPC . G06T 2207/10016; G06T 2207/10081; G06T 2207/10088; G06T 2207/10116; G06T 5/003; A61B 5/08; A61B 6/486; A61B 6/5264
See application file for complete search history.

(56) References Cited

U.S. PATENT DOCUMENTS 7,386,157 B2 * 6/2008 Tago ..................... G06T 7/2053
382/130
8,433,159 B1 * 4/2013 Nord ..................... G06T 7/2066
375/240.16

(Continued)

FOREIGN PATENT DOCUMENTS

CN 103479375 A 1/2014
WO WO 2014/001946 A1 1/2014

OTHER PUBLICATIONS

Office Action for corresponding Chinese patent application 20150098428.9 dated Feb. 4, 2017 (8 pages), including English translation (10 pages).
(Continued)

*Primary Examiner* — Bhavesh Mehta
*Assistant Examiner* — Ian Lemieux
(74) *Attorney, Agent, or Firm* — Brinks Gilson & Lione

(57) ABSTRACT

An image processing device includes an acquiring unit configured to acquire a medical video image obtained by imaging of lungs, a holding unit configured to hold a lung field motion model, the lung field motion model simulating lung field motion, and a processing unit configured to process the medical video image by using the lung field motion model.

20 Claims, 13 Drawing Sheets

(51) Int. Cl.
*A61B 5/08* (2006.01)
*A61B 6/00* (2006.01)
*G06T 7/20* (2017.01)
*G06T 5/00* (2006.01)
*G06T 7/246* (2017.01)
*G06T 7/254* (2017.01)

(52) U.S. Cl.
CPC .............. *G06T 2207/10016* (2013.01); *G06T 2207/10081* (2013.01); *G06T 2207/10088* (2013.01); *G06T 2207/10116* (2013.01); *G06T 2207/10132* (2013.01); *G06T 2207/30061* (2013.01)

(56) References Cited

U.S. PATENT DOCUMENTS

| | | | | |
|---|---|---|---|---|
| 2009/0034819 | A1* | 2/2009 | Nord | A61B 6/04 |
| | | | | 382/132 |
| 2011/0170658 | A1* | 7/2011 | Arakita | A61B 6/032 |
| | | | | 378/8 |
| 2012/0300904 | A1 | 11/2012 | Shimada et al. | |
| 2013/0331725 | A1* | 12/2013 | Noji | A61B 6/5217 |
| | | | | 600/534 |

OTHER PUBLICATIONS

Office Action for corresponding Japanese patent application 2014-045084 dated Jun. 26, 2017, 3 pages, including English language translation thereof, 5 pages.

* cited by examiner

UPRIGHT POSITION

DECUBITUS POSITION

LUNG HILA

APICAL PORTIONS OF LUNGS

IMAGE PROCESSING DEVICE, IMAGING SYSTEM, AND IMAGE PROCESSING PROGRAM

The entire disclosure of Japanese Patent Application No. 2014-045084 filed on Mar. 7, 2014 including description, claims, drawings, and abstract are incorporated herein by reference in its entirety.

BACKGROUND OF THE INVENTION

Field of the Invention

The present invention relates to processing of medical video images.

Description of the Related Art

In imaging of a chest X-ray video image, X-rays are generated from an X-ray tube, the generated X-rays are caused to pass through a human body, and the X-rays having passed through the human body are detected by a flat panel detector (FPD), for example. A chest X-ray video image is generated to aid a medical doctor in diagnosing a patient, for example.

US 2012/0300904 A discloses a technology for processing chest X-ray video images. In the technology disclosed in the above publication, a difference value between the pixels located in the same positions in one frame image and another frame image is determined so as to detect abnormality in respiration (ventilation) or the blood flow in the chest region.

Since the lung field moves, even when the difference value between the pixels located in the same positions in one frame image and another frame image is determined, the difference value is not necessarily a difference value between pixels showing the same object, and an appropriate difference image is not necessarily generated.

This problem is also caused in a case where processing other than difference image generation is performed, or where a medical video image is generated by an imaging technology other than radiography, for example.

SUMMARY OF THE INVENTION

The present invention has been made to solve the above problem. An object of the present invention is to reduce the influence of lung field motion on processing of medical video images, and appropriately process medical video images, regardless of lung field motion.

To achieve the abovementioned object, according to an aspect, an image processing device reflecting one aspect of the present invention comprises an acquiring unit configured to acquire a medical video image obtained by imaging of lungs, a holding unit configured to hold a lung field motion model, the lung field motion model simulating lung field motion, and a processing unit configured to process the medical video image by using the lung field motion model.

The above and other objects, features, aspects, and advantages of the present invention will be made more apparent below by the detailed description of the present invention in conjunction with the accompanying drawings.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein.

DESCRIPTION OF THE PREFERRED EMBODIMENTS

Hereinafter, an embodiment of the present invention will be described with reference to the drawings. However, the scope of the invention is not limited to the illustrated examples.

(1) First Embodiment
(1.1) Imaging System
A first embodiment relates to an imaging system.
The block diagram in FIG. 1 shows an imaging system of the first embodiment.

Figure 1:
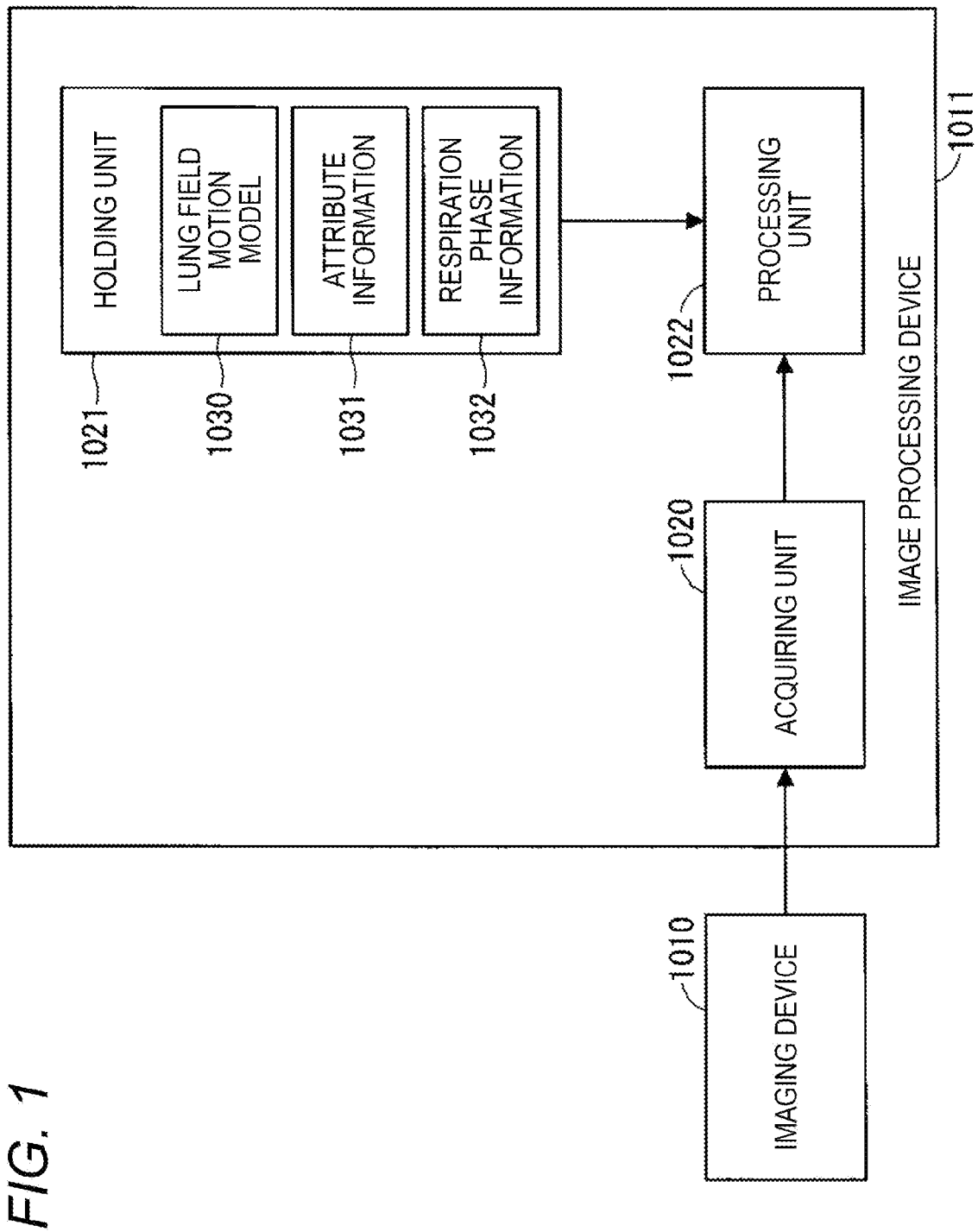
FIG. 1 is a block diagram of an imaging system.

The imaging system 1000 shown in FIG. 1 includes an imaging device 1010 and an image processing device 1011.

The imaging device 1010 generates medical video images by radiography. The imaging device 1010 generates X-rays from an X-ray tube, causes the generated X-rays to penetrate through a human body, and detects the X-rays having penetrated through the human body with a flat panel detector (FPD). With this, the imaging device 1010 images structures in the human body, and generates a frame image showing the structures in the human body. The imaging device 1010 performs imaging twice or more, and generates a medical video image including two or more frame images. A medical video image is a two-dimensional image, and is digital data. Alternatively, the imaging device 1010 may generate a medical video image by a technology other than radiography. For example, the imaging device 1010 may generate a medical video image by ultrasonic imaging, magnetic resonance imaging (MRI), computerized tomography (CT), or the like. The imaging device 1010 may image structures in the body of a creature other than a human. A medical video image may be a three-dimensional video image.

The image processing device 1011 acquires a medical video image generated by the imaging device 1010, and processes the acquired medical video image. The medical video image to be processed is a chest X-ray video image that is obtained by imaging of human lungs. Alternatively, the medical video image to be processed may be obtained by imaging of the lungs of a creature other than a human.

(1.2) Image Processing Device

The image processing device 1011 includes an acquiring unit 1020, a holding unit 1021, and a processing unit 1022.

The acquiring unit 1020 performs communication, and acquires a medical video image directly from the imaging device 1010, or from the imaging device 1010 via a device other than the imaging device 1010, such as an image server. Alternatively, the acquiring unit 1020 may acquire a medical video image by reading a recording medium such as an optical disk having the medical video image recorded thereon.

The holding unit 1021 holds two or more lung field motion models 1030, attribute information 1031, respiration phase information 1032, and the like. In some cases, the holding unit 1021 holds only one lung field motion model. In some cases, the holding unit 1021 holds neither the attribute information 1031 nor the respiration phase information 1032 or holds either one of them.

The two or more lung field motion models 1030 each simulate motion of a lung field. In some cases, the two or more lung field motion models 1030 each simulate the instantaneous motion of a lung field. In other cases, the two or more lung field motion models 1030 each simulate the motion of a lung field over a period of time. A lung field motion model indicates a relationship between positions in a frame image and the motion of a lung field. The motion of a lung field means both the size and the direction of the motion of a lung field. The motion of a lung field means only either the size or the direction of the motion of a lung field in some cases.

The attribute information 1031 is information with which respective attributes of the two or more lung field motion models 1030 can be identified.

The respiration phase information 1032 is information with which the respective respiration phases corresponding to the two or more lung field motion models 1030 can be identified.

The processing unit 1022 generates a difference image between one frame image and the other frame image, using lung field motions simulated by the two or more lung field motion models 1030. A lung field motion model is used for reducing the influence of a shift between a position shown in the one frame image and the position shown in the other frame image. With this, the influence of a lung field motion on generation of a difference image is reduced, and a difference image is appropriately generated, regardless of the motion of the lung field. A lung field motion may be used in a process other than a difference image generation process. The other frame image is typically the frame image generated after the one frame image is generated. However, the other frame image may not be the frame image generated after the one frame image is generated.

(1.3) Computer

Figure 2:
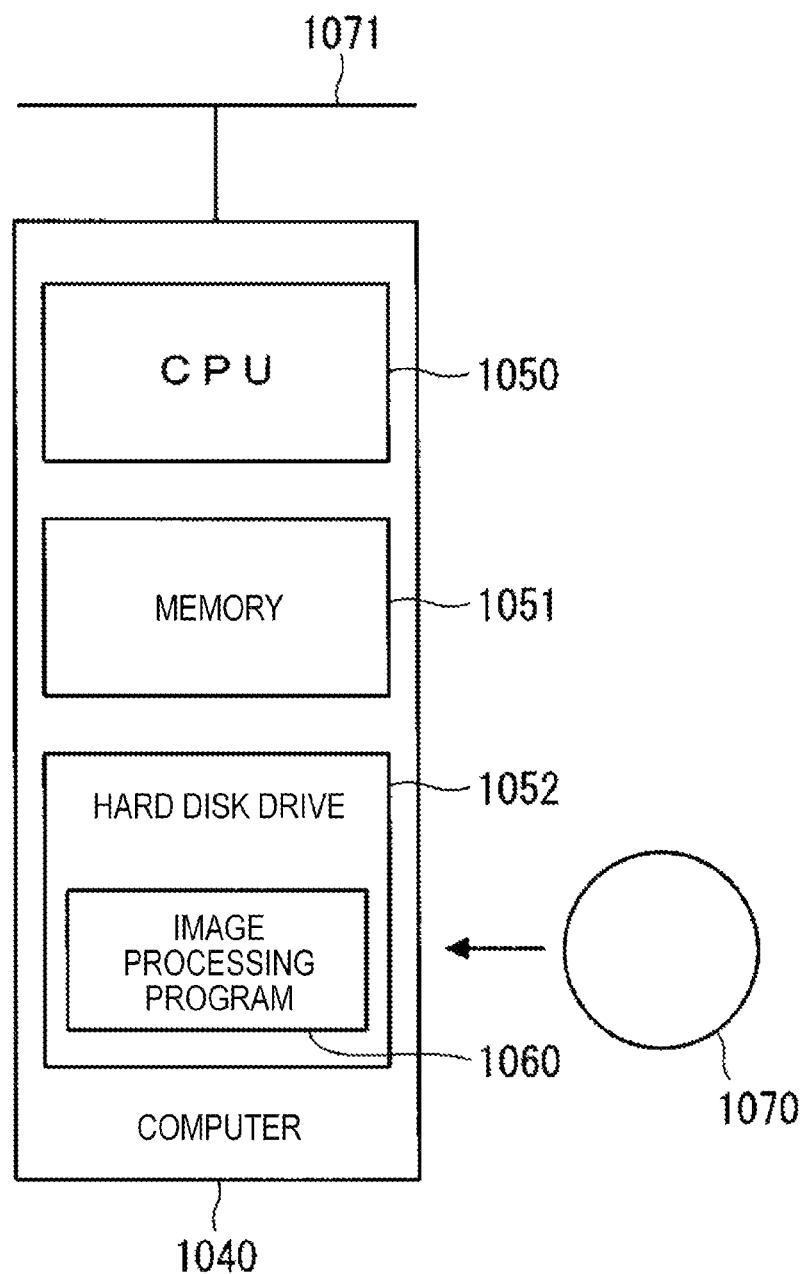
FIG. 2 is a block diagram of a computer.

FIG. 2 is a block diagram of a computer.

The computer 1040 shown in FIG. 2 includes a CPU 1050, a memory 1051, and a hard disk drive 1052, and serves as the image processing device 1011. The hard disk drive 1052 may be replaced with an auxiliary storage device of some other kind. An image processing program 1060 is installed into the hard disk drive 1052. The functions of the image processing device 1011 are realized by the CPU 1050 loading the image processing program 1060 into the memory 1051 and executing the image processing program 1060. All of or some of the functions of the image processing device 1011 may be realized by hardware that does not involve software. All of or some of the functions of the image processing device 1011 may be realized by two or more computers. The image processing program 1060 may be pre-installed into the hard disk drive 1052 prior to shipment of the computer 1040, or may be installed into the hard disk drive 1052 after shipment of the computer 1040. The image processing program 1060 may be installed by reading of a recording medium 1070 such as an optical disk having the image processing program 1060 recorded thereon, or may be installed by downloading via a network 1071.

(1.4) Lung Field Motion Model

The two or more lung field motion models 1030 may represent a lung field motion difference due to spatial positions, may represent a lung field motion difference due to respiration phases, or may represent a lung field motion difference due to attributes. An attribute is information that affects the motion of a lung field. Examples of attributes include the body position at the time of imaging, a physiological feature point, the age of the imaged person, the sex of the imaged person, the shape of the body of the imaged person, the type of the disease the imaged person has contracted, the severity of the disease the imaged person has contracted, and the like. The body position may be an upright position, a decubitus position, or the like. The shape of the body is identified by the percentage of body fat, the chest circumference, the abdominal circumference, the body thickness, and the like.

In a case where the two or more lung field motion models 1030 each indicate a relationship between positions in a frame image and the motion of a lung field, a lung field motion difference due to spatial positions is represented by each of the two or more lung field motion models 1030, a lung field motion difference due to respiration phases is represented as a difference between the lung field motion indicated by one lung field motion model and the lung field motion indicated by the other lung field motion model, and a lung field motion difference due to attributes is represented as a lung field motion difference between the lung field motion indicated by the one lung field motion model and the lung field motion indicated by the other lung field motion model.

(1.5) Lung Field Motion Difference Due to Positions in the Vertical Position (Gravity Direction)

Figure 3:
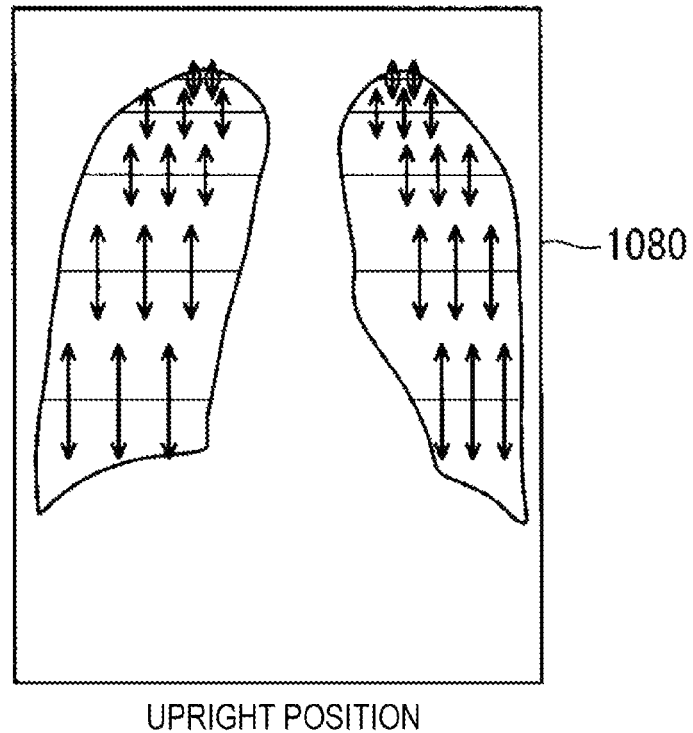
FIG. 3 is a schematic view of a lung field motion model.
Figure 4:
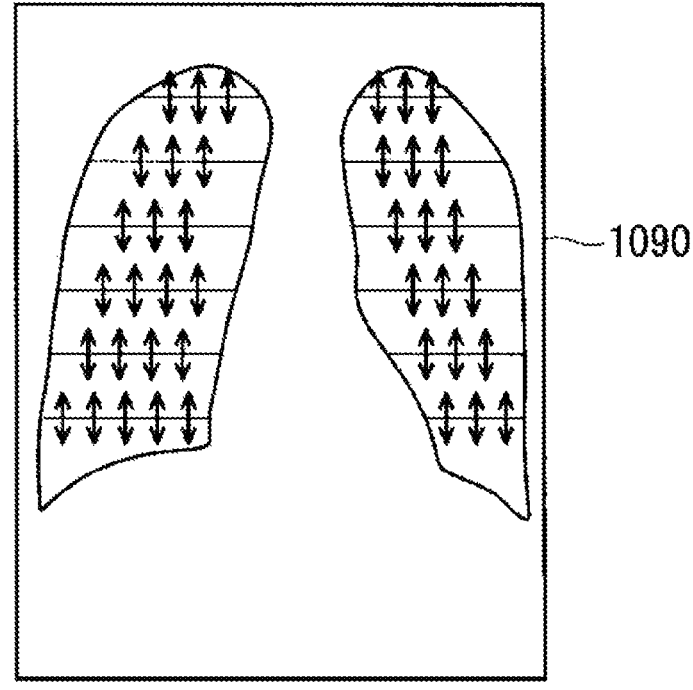
FIG. 4 is a schematic view of another lung field motion model.

The schematic view in FIG. 3 and the schematic view in FIG. 4 each show a lung field motion model.

The lung field motion model 1080 shown in FIG. 3 and the lung field motion model 1090 in shown FIG. 4 each show a relationship between positions in a frame image and the motion of the lung field. In each of the lung field motion models 1080 and 1090, positions in the frame image are represented by the positions of arrows, the direction of the motion of the lung field is represented by the direction of the arrows, and the size of the motion of the lung field is represented by the lengths of the arrows. This aspect is the same as in the lung field motion models shown in other schematic views. The lung field motion model 1080 is a model in a case where the body position is an upright position. The lung field motion model 1090 is a model in a case where the body position is a decubitus position.

In some cases, the motion of the lung field is considered to vary with positions in the vertical direction. For example, the motion of the lung field is considered to be larger toward a lower location in the vertical direction.

In a case where the body position at the time of imaging is an upright position, the up and down direction of frame image is a direction parallel to the vertical direction, and the left and right direction of the frame image is a direction perpendicular to the vertical direction. Therefore, when the motion of the lung field is considered to be larger toward a lower location in the vertical direction, the motion of the lung field is considered to be larger toward a lower location in the frame image. Accordingly, when the body position at the time of imaging is an upright position, the lung field motion model 1080 in which the motion of the lung field is larger toward a lower location can be created.

In a case where the body position at the time of imaging is a decubitus position, the up and down direction and the left and right direction of the frame image are directions perpendicular to the vertical direction, and therefore, the motion of the lung field in the frame image is considered to be uniform. Accordingly, when the body position at the time of imaging is a decubitus position, the lung field motion model 1090 in which the motion of the lung field is uniform can be created.

The lung field motion difference due to positions in the vertical direction is represented by each of the lung field motion models 1080 and 1090. The lung field motion difference due to body positions is represented as a difference between the lung field motion indicated by the lung field motion model 1080 and the lung field motion indicated by the lung field motion model 1090.

A lung field motion model can also be created in a case where the body position at the time of imaging is neither an upright position nor a decubitus position. For example, a lung field motion model can also be created in a case where the body position at the time of imaging is a lateral decubitus position. As the number of lung field motion models is increased, the imaging conditions to be satisfied can be increased.

Figure 5:
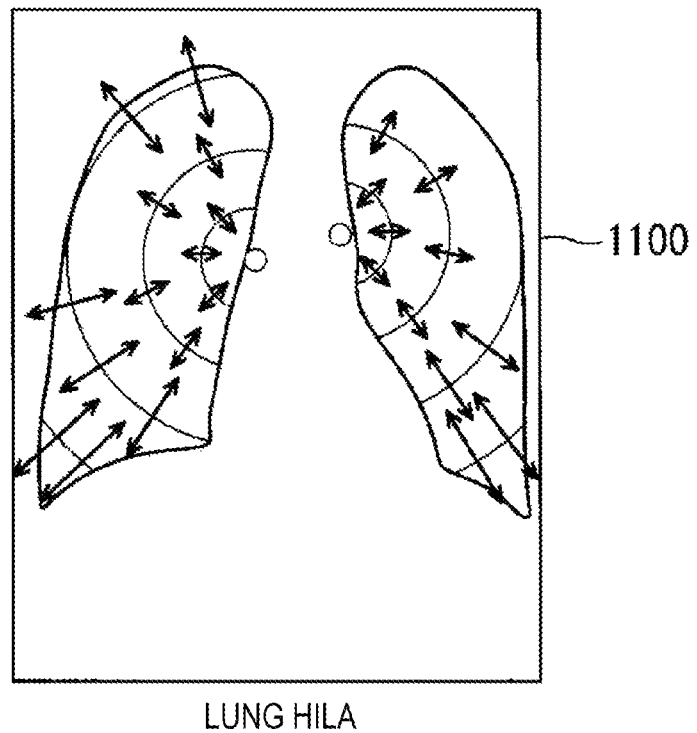
FIG. 5 is a schematic view of yet another lung field motion model.
Figure 6:
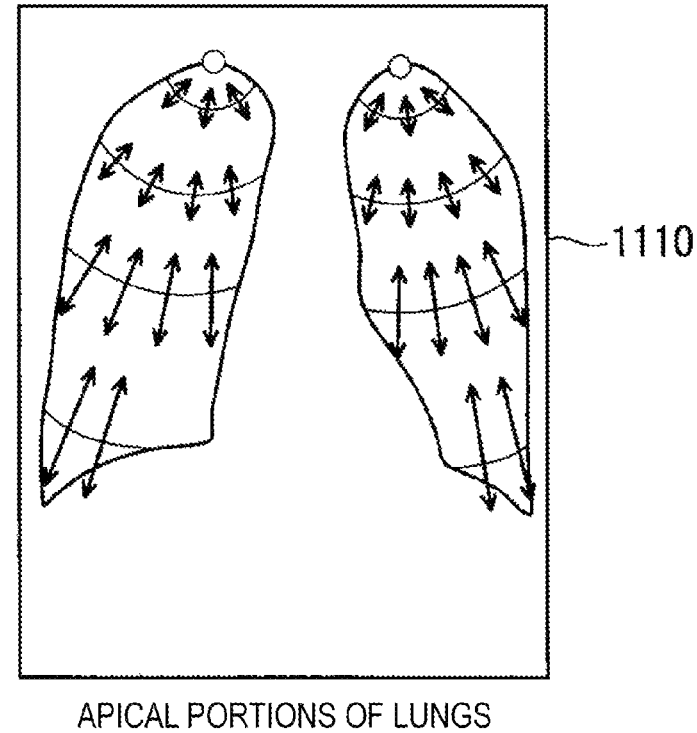
FIG. 6 is a schematic view of still another lung field motion model.

(1.6) Lung Field Motion Difference Due to Distances from Physiological Feature Points The schematic view in FIG. 5 and the schematic view in FIG. 6 each show a lung field motion model.

The lung field motion model 1100 in shown FIG. 5 and the lung field motion model 1110 shown in FIG. 6 each show a relationship between positions in a frame image and the motion of the lung field. The lung field motion model 1100 is a model in a case where the physiological feature points are the lung hila. The lung field motion model 1110 is a model in a case where the physiological feature points are the apical portions of the lungs.

In some cases, the motion of the lung field is considered to vary with distances from the physiological feature points. In some cases, the motion of the lung field is considered to be larger at a location further away from the physiological feature points, for example. Accordingly, when the physiological feature points are the lung hila, the lung field motion model 1100 in which the motion of the lung field is larger in a direction further away from the lung hila can be created. When the physiological feature points are the apical portions of the lungs, the lung field motion model 1110 in which the motion of the lung field is larger in a direction further away from the apical portions of the lungs can be created. It can be understood from the mechanism of the lung field that the motion of the lung field becomes larger in a direction further away from the lung hila. The blood vessels in the lung field are thinner in a direction further away from the lung hila. The motions of the blood vessels in the lung field caused by the motion of the lung field are larger as blood vessels become thinner. Therefore, when attention is paid to the motions of the blood vessels, it can be said that the motion of the lung field is larger in a direction further away from the lung hila.

The lung field motion difference due to distances from the physiological feature points is represented by each of the lung field motion models 1100 and 1110. The lung field motion difference due to the physiological feature points is represented as a difference between the lung field motion indicated by the lung field motion model 1100 and the lung field motion indicated by the lung field motion model 1110.

(1.7) Information for Identifying a Spatial Position

A position in the vertical direction and a distance from a physiological feature point are both information for identifying a spatial position. Instead of a position in the vertical direction and a distance from a physiological feature point, it is possible to use some other information for identifying a spatial position.

(1.8) Lung Field Motion Difference Due to Respiration Phases

Figure 7:
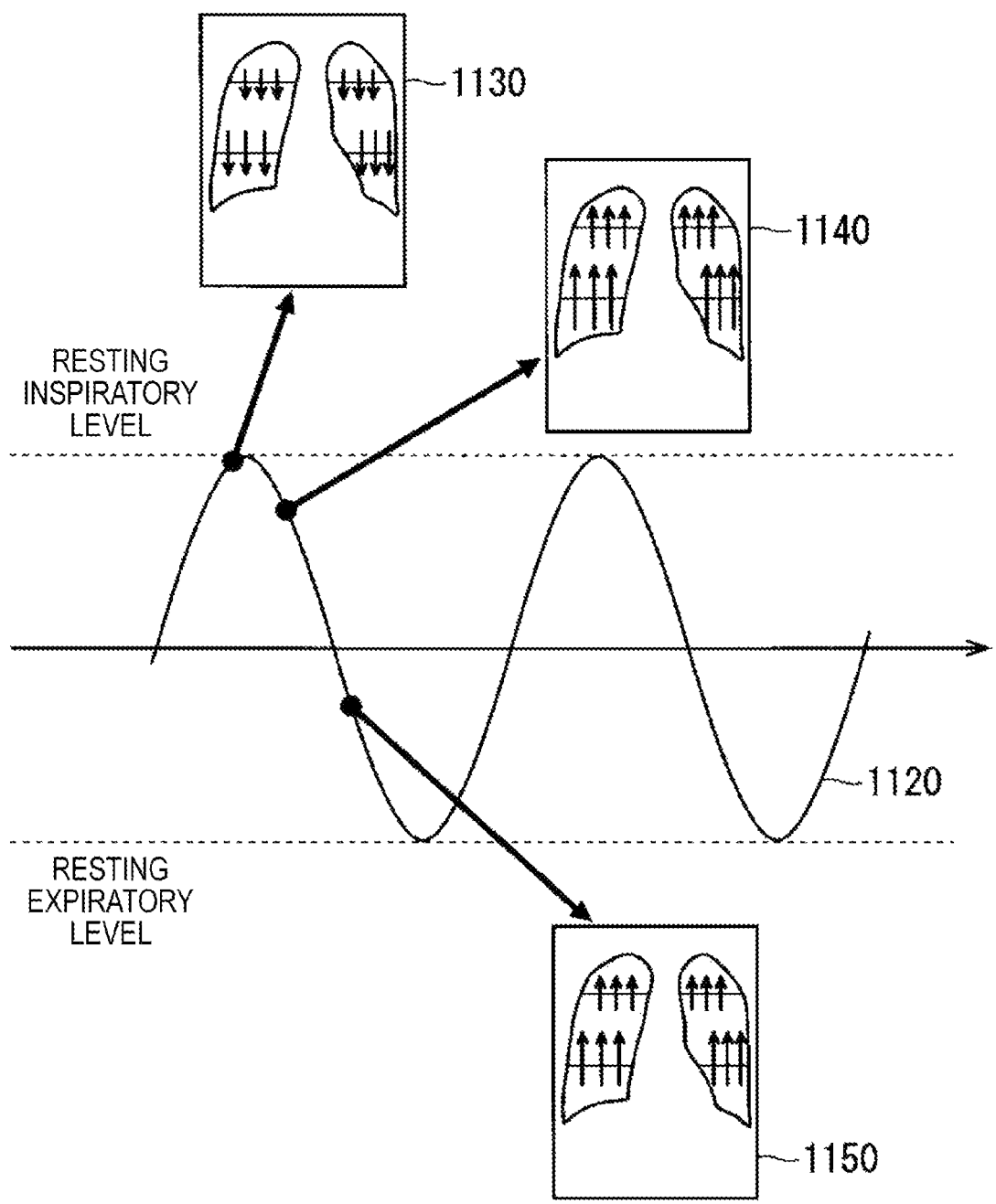
FIG. 7 is a schematic view of a respiration curve and lung field motion models.

The schematic view in FIG. 7 shows a respiration curve and lung field motion models.

The respiration curve 1120 shown in FIG. 7 is a graph representing a variation in the amount of air in the lungs over time, with the abscissa axis indicating time, the ordinate axis indicating the amount of air in the lungs. The lung field motion models 1130, 1140, and 1150 shown in FIG. 7 each show a relationship between positions in a frame image and the motion of the lung field. The lung field motion model 1130 is a model in a case where the respiration phase is close to the resting inspiratory level. The lung field motion model 1140 is a model in a case where the respiration phase is in an inspiratory period, and is relatively close to the resting inspiratory level. The lung field motion model 1150 is a model in a case where the respiration phase is in an expiratory period, and is relatively far away from the resting expiratory level.

The motion of the lung field varies with respiration phases. In a case where natural respiration is conducted, and the respiration phase is close to the resting expiratory level or the resting inspiratory level, the motion of the lung field is relatively small. In a case where forced respiration is conducted and the respiration phase is in the inspiratory period immediately after a maximal expiratory level, or where the respiration phase is in the expiratory period immediately after a maximal inspiratory level, the motion of the lung field is large. Accordingly, a lung field motion model can be created for each respiration phase. A lung field motion model created for a respiration phase may represent a lung field motion difference due to positions in the vertical direction as shown in FIG. 7, or may represent a lung field motion difference due to distances from a physiological feature point, which is a different case from the case shown in FIG. 7.

These lung field motion models can be appropriately selected in accordance with the conditions for imaging, the object to be observed, a selected frame image, or the like.

(1.9) Processing

Figure 8:
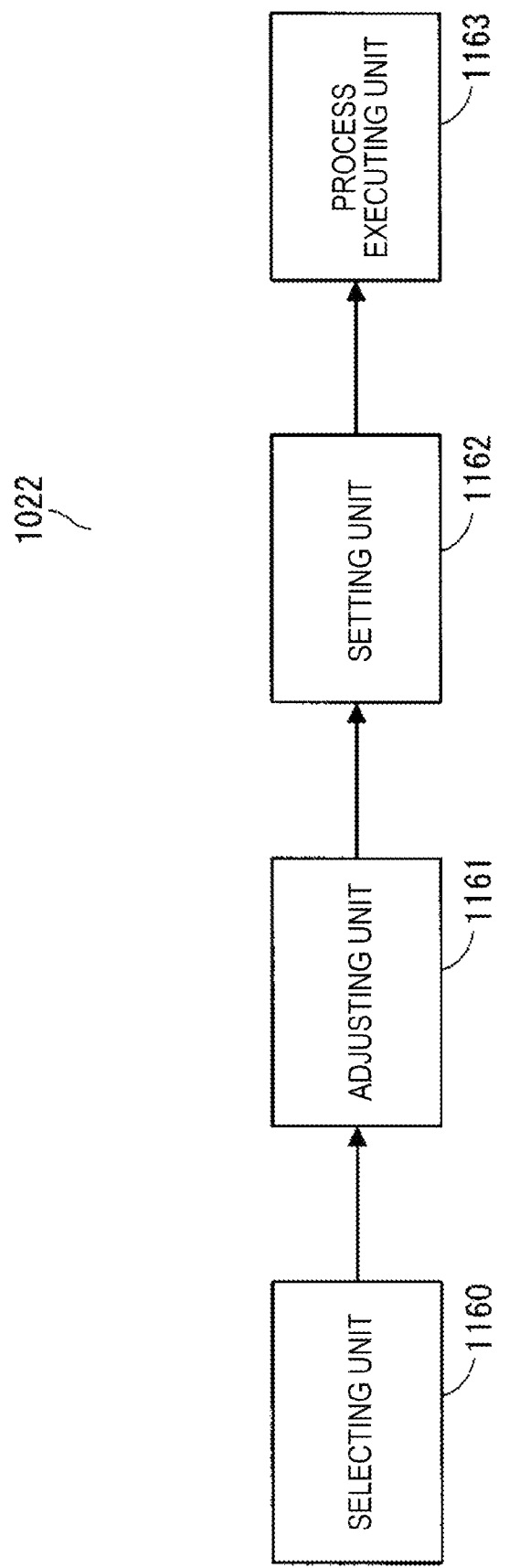
FIG. 8 is a block diagram of a processing unit of a first embodiment.
Figure 9:
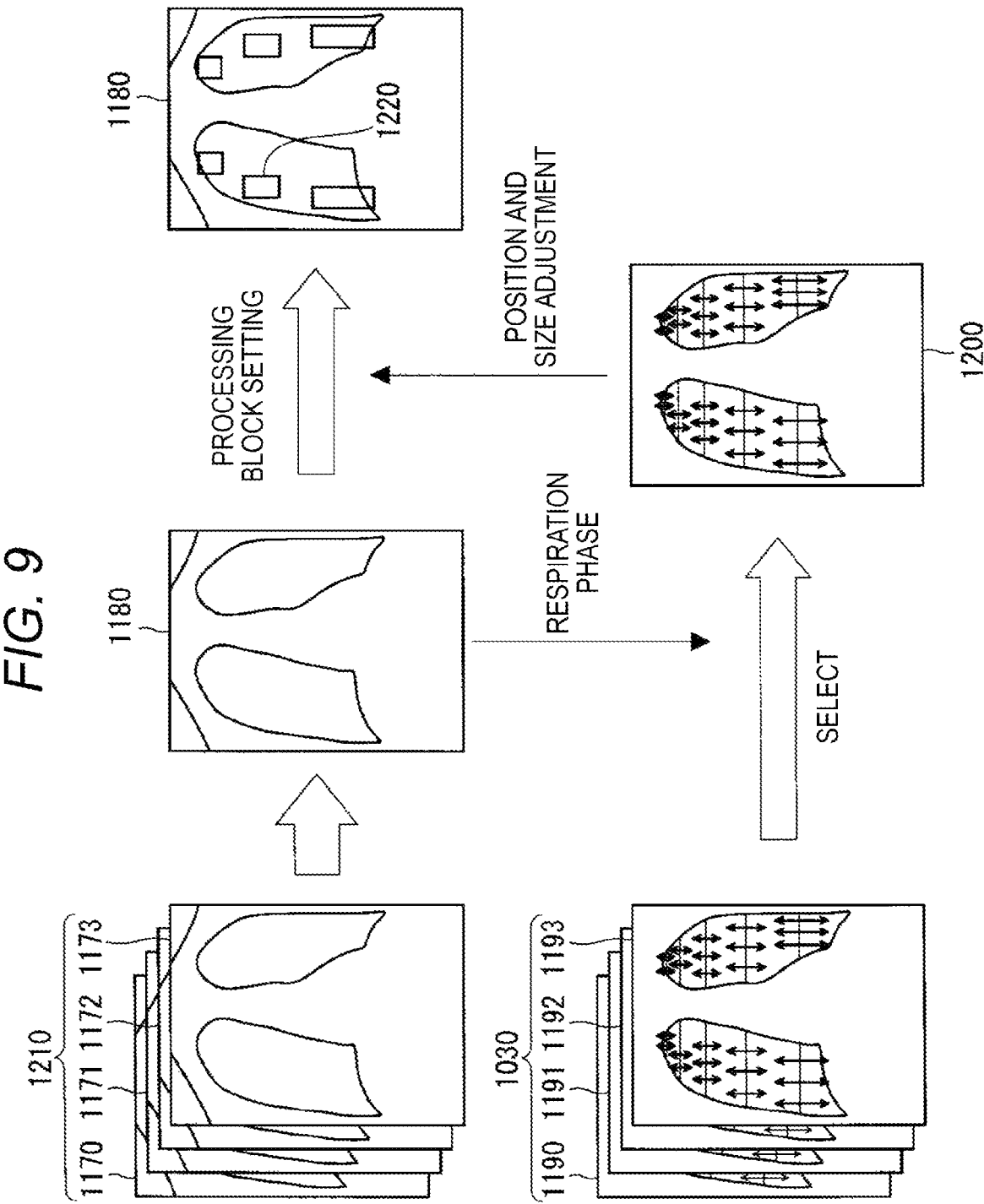
FIG. 9 is a schematic view showing an example of processing according to the first embodiment.

The block diagram in FIG. 8 shows the processing unit of the first embodiment. The schematic view in FIG. 9 shows an example of processing to be performed by the processing unit of the first embodiment. The example of the processing shown in FIG. 9 is to be performed in a case where the medical video image includes four frame images, the holding unit has four lung field motion models, and lung field motion models each expressing a lung field motion difference due to positions in the vertical direction have been prepared for the respective respiration phases. The number of the frame images included in the medical video image, the number of the lung field motion models held in the holding unit, and the prepared lung field motion models may differ from those shown in FIG. 9.

The processing unit 1022 shown in FIG. 8 includes a selecting unit 1160, an adjusting unit 1161, a setting unit 1162, and a process executing unit 1163.

The selecting unit 1160 identifies the respiration phase at the time when a frame image 1180 selected from among frame images 1170, 1171, 1172, and 1173 sequentially is generated, and selects the lung field motion model 1200 corresponding to the identified respiration phase from among lung field motion models 1190, 1191, 1192, and 1193 by referring to the respiration phase information 1032. The respiration phase is identified through an analysis of the frame image 1180. For example, the respiration phase is identified from the position in which the diaphragm is shown in the frame image 1180, the area of the region where the lung field is shown in the frame image 1180, or the like. In a case where the ventilation volume is measured during the imaging, the respiration phase may be identified from the ventilation volume. The respiration phase may be identified from an input from the operator. In a case where only one lung field motion model is held, only the frame image of the respiration phase corresponding to the one lung field motion model is processed.

The adjusting unit 1161 adjusts the position and the size of the lung field motion model 1200 to those of the frame image 1180. As the positions and the sizes are adjusted with respect to the respective frame images 1170, 1171, 1172, and 1173, the positions and the sizes of the lung field motion models 1190, 1191, 1192, and 1193 are adjusted to those of a medical video image 1210. As the position and the size of the lung field motion model 1200 are adjusted, the respective pixels constituting the frame image 1180 are associated with the lung field motions simulated by the lung field motion model 1200. In a case where the association can be conducted without any adjustment of the position and the size of the lung field motion model 1200, the adjustment of the position and the size of the lung field motion model 1200 may be omitted.

The setting unit 1162 sets processing blocks 1220 in the frame image 1180. The processing blocks 1220 are regions for performing arithmetic processing (such as statistical processing) on the pixel values included in the processing blocks 1220. The processing blocks 1220 are set on the respective pixels constituting the frame image 1180, and are set by using the lung field motions associated with the pixels. Preferably, the orientations of the processing blocks 1220 are adjusted to the directions of the lung field motions, the processing blocks 1220 are made larger in the directions of the processing block motions as the lung field motions become larger, and as a result, the processing blocks 1220 are made larger as the lung field motions become larger. The processing blocks 1220 may be set in accordance only with the sizes of the lung field motions. For example, the orientations of the processing blocks 1220 may be fixed, though the processing blocks 1220 are made larger as the lung field motions become larger. The processing blocks 1220 may be set in accordance only with the directions of the lung field motions. For example, the sizes of the processing blocks 1220 may be fixed, though the orientations of the processing blocks 1220 are adjusted to the directions of the lung field motions.

In a case where the orientations of the processing blocks 1220 are adjusted to the directions of the lung field motions, the angles formed by the orientations of the processing blocks 1220 and the directions of the lung field motions are within a predetermined range from 0 or 180 degrees, or preferably, 0 or 180 degrees.

The processing blocks 1220 each have a rectangular shape, and the orientations of the processing blocks 1220 are the respective long-side directions thereof. The processing blocks 1220 may not have rectangular shapes. For example, the processing blocks 1220 may have elliptical shapes. In a case where the processing blocks 1220 each have an elliptical shape, the orientations of the processing blocks 1220 are the respective long-axis directions thereof. More generally, the orientation of a processing block 1220 is the longitudinal direction of the processing block 1220. Alternatively, each of the processing blocks 1220 may have a circular shape, a square shape, or the like.

Figure 10:
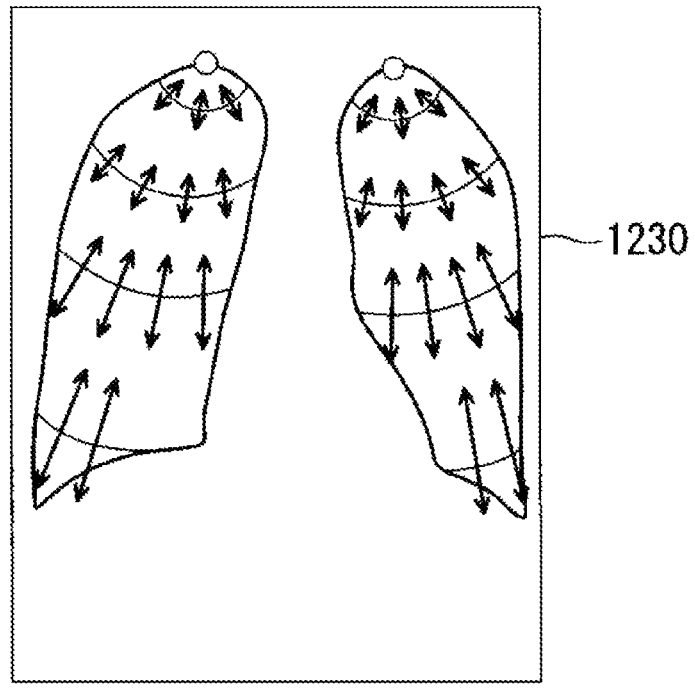
FIG. 10 is a schematic view of a lung field motion model.
Figure 11:
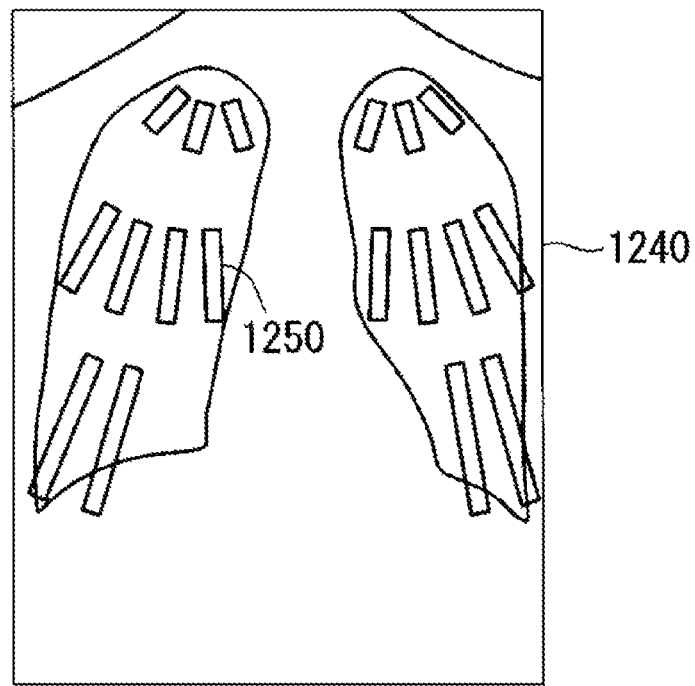
FIG. 11 is a schematic view of a frame image.

The schematic view in FIG. 10 shows a lung field motion model. The schematic view in FIG. 11 shows a frame image.

The lung field motion model 1230 shown in FIG. 10 represents lung field motion differences due to distances from the apical portions of the lungs. In the frame image 1240 shown in FIG. 11, processing blocks 1250 are set by using the lung field motions simulated by the lung field motion model 1230.

Even in a case where the lung field motion model 1230 represents lung field motion differences due to distances from the apical portions of the lungs, the orientations of the processing blocks 1250 are preferably adjusted to the directions of the lung field motions, the processing blocks 1250 are made larger in the directions of the processing block motions as the lung field motions become larger, and as a result, the processing blocks 1250 are made larger as the lung field motions become larger.

The process executing unit 1163 generates a difference image between one frame image and the other frame image, the one frame image being the frame image 1180, the other frame image being the frame image generated after the frame image 1180. In the generation of the difference image, the pixels corresponding to the respective pixels constituting the one frame image are identified from among the pixels constituting the other frame image, the difference values between the respective pixels constituting the one frame image and the corresponding pixels are determined, and the difference values are set as the pixel values of the pixels constituting the difference image. In a case where difference values are determined, the pixels corresponding to the respective pixels included in the processing blocks are identified from among the pixels constituting the other frame image, the pixel value differences between the respective pixels included in the processing blocks and the corresponding pixels are determined, and the mean value of the pixel value differences is set as the difference value with respect to the pixels on which the processing blocks 1220 are set. The mean value may be replaced with a representative value of some other kind. For example, the mean value may be replaced with an intermediate value. The processing blocks 1220 each including two or more pixels are used, and the representative values of the pixel difference values in the processing blocks 1220 are set as the difference values. Accordingly, in a case where the pixels located in the same positions among the frame images are the corresponding pixels, the influence of the lung field motions on the difference values can be reduced.

A difference image only between regions where the lung field is shown may be generated. In a case where a difference image only between regions where the lung field is shown is generated, the regions where the lung field is shown are extracted from the frame images.

(2) Second Embodiment

A second embodiment relates to a processing unit that replaces the processing unit of the first embodiment.

Figure 12:
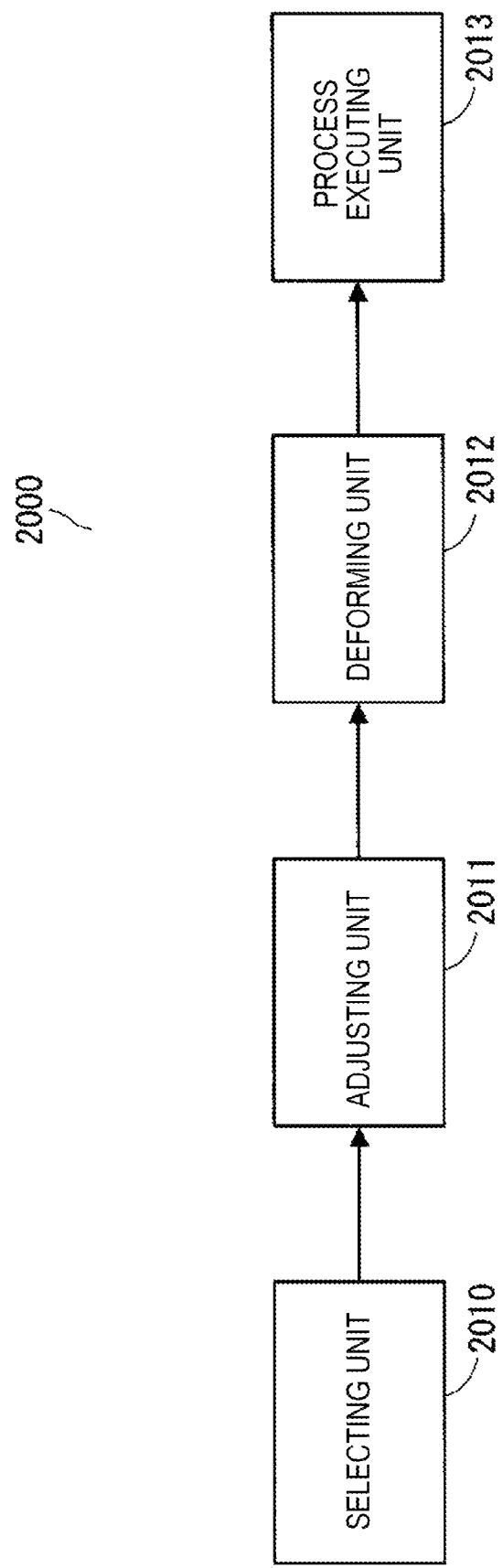
FIG. 12 is a block diagram of a processing unit of a second embodiment.
Figure 13:
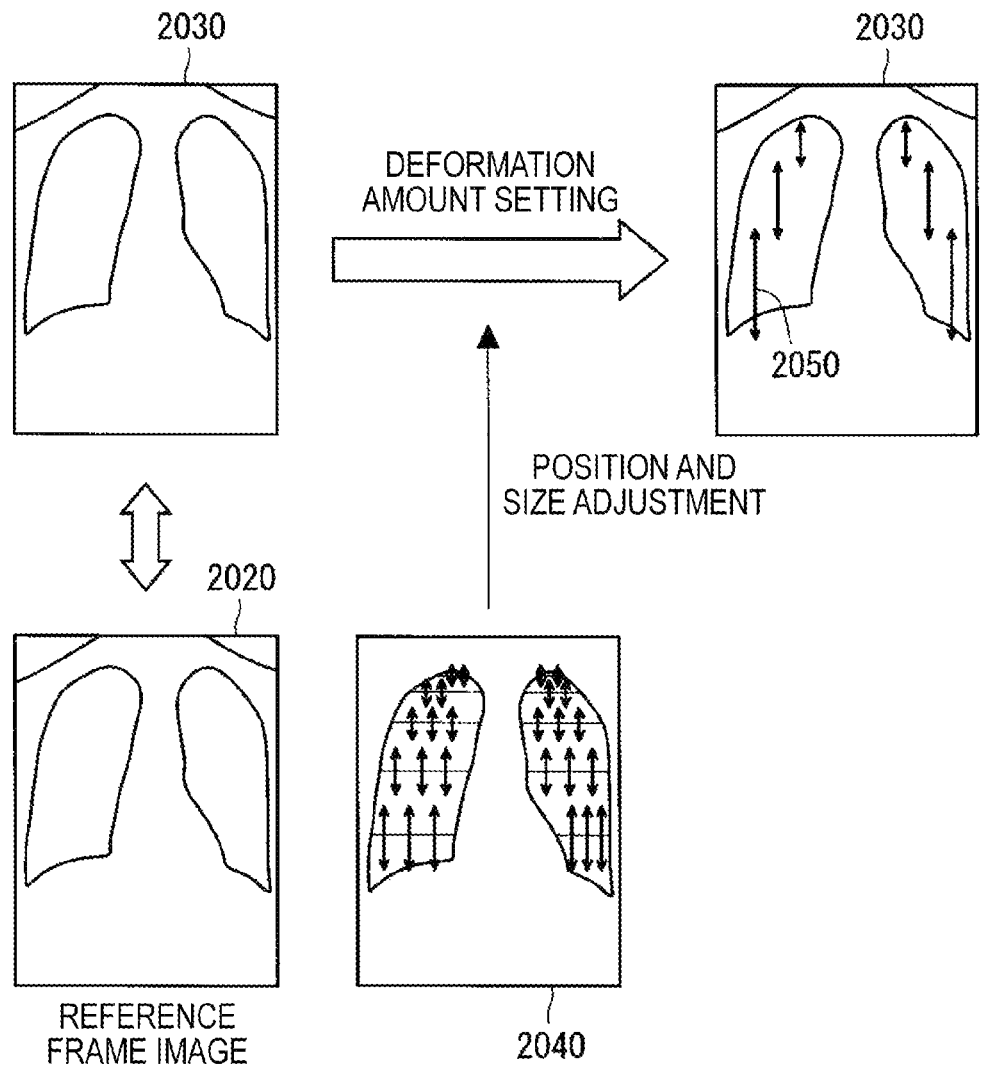
FIG. 13 is a schematic view showing an example of processing according to the second embodiment.
Figure 14:
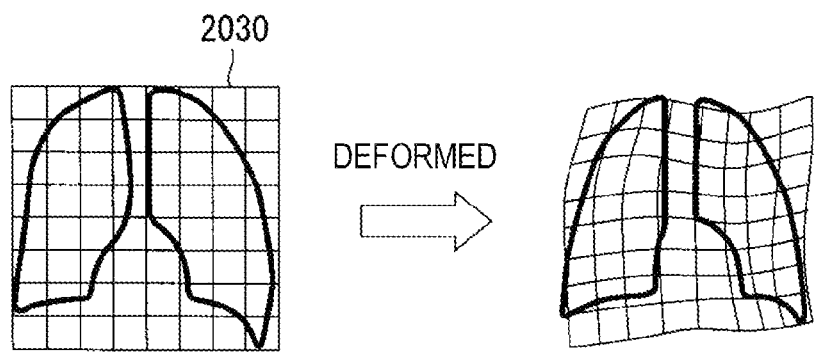
FIG. 14 is a schematic view of example deformation of a frame image.

The block diagram in FIG. 12 shows the processing unit of the second embodiment. The schematic view in FIG. 13 shows an example of processing to be performed by the processing unit of the second embodiment. FIG. 14 is a schematic view of example deformation of a frame image. The example processing shown in FIG. 13 is to be performed in a case where lung field motion models representing lung field motion differences due to positions in the vertical direction are prepared for respective attributes. The prepared lung field motion models may differ from those shown in FIG. 13.

The processing unit 2000 shown in FIG. 12 includes a selecting unit 2010, an adjusting unit 2011, a deforming unit 2012, and a process executing unit 2013.

The selecting unit 2010 identifies the attribute of a medical video image, and selects the lung field motion model 2040 corresponding to the identified attribute from between two or more lung field motion model 1030 by referring to attribute information 1031. The attribute may be identified through an analysis carried out by the image processing device 1011, may be identified from the metadata attached to the medical video image, or may be identified from an input from the operator. The analysis may be a blood flow analysis, a respiration analysis, or the like. In a case where only one lung field motion model is held, a medical video image having the attribute corresponding to the one lung field motion model is generated and processed.

The adjusting unit 2011 adjusts the position and the size of the lung field motion model 2040 to a frame image 2030 sequentially selected from two or more frame images. As the position and the size are adjusted with respect to the two or more frame images, the position and the size of the lung field motion model 2040 are adjusted to those of the medical video image. As the position and the size of the lung field motion model 2040 are adjusted, the respective pixels constituting the frame image 2030 are associated with the lung field motions simulated by the lung field motion model 2040.

The deforming unit 2012 sets deformation amounts 2050 for the frame image 2030, and deforms the medical video image by deforming the frame image 2030 in conformity with a reference frame image 2020, with the deformation amounts 2050 being the constraint conditions. With this, the pixels constituting one frame image are associated with the pixels constituting the other frame image. Alternatively, the frame image 2030 may be deformed in conformity with the frame image generated immediately before the frame image 2030.

The deformation amounts 2050 are set for the respective pixels constituting the frame image 2030, and are set by using the lung field motions associated with the pixels. The directions of deformation are adjusted to the directions of the lung field motions. Preferably, the deformation amounts 2050 are made larger as the lung field motions become larger.

In the deformation process, the frame image 2030 is divided in a grid-like pattern as shown in FIG. 14, and local shift amounts are determined through local matching. The shift amounts are determined, with the set deformation amounts 2050 being the constraint conditions. As the deformation amounts 2050 become larger, greater deformation is allowed. The deformation algorithm may be changed, or the usage of the lung field motion model 2040 in the deformation process may be changed.

The process executing unit 2013 generates a difference image between deformed one frame image and the other frame image, the one frame image being the frame image 2030, the other frame image being the frame image generated after the frame image 2030. In the generation of the difference image, the pixels corresponding to the respective pixels constituting the one frame image are identified from among the pixels constituting the other frame image, the difference values as the pixel value differences between the respective pixels constituting the one frame image and the corresponding pixels are determined, and the difference values are set as the pixel values of the pixels constituting the difference image. The pixels located in the same positions may be regarded as the corresponding pixels. This is because the frame image has been deformed, and the influence of the lung field motions has already been reduced, even if the pixels located in the same positions are regarded as the corresponding pixels. Alternatively, a difference image may be generated with the use of processing blocks as in the first embodiment.

(3) Third Embodiment

A third embodiment relates to a processing unit that replaces the processing unit of the first embodiment.

Figure 15:
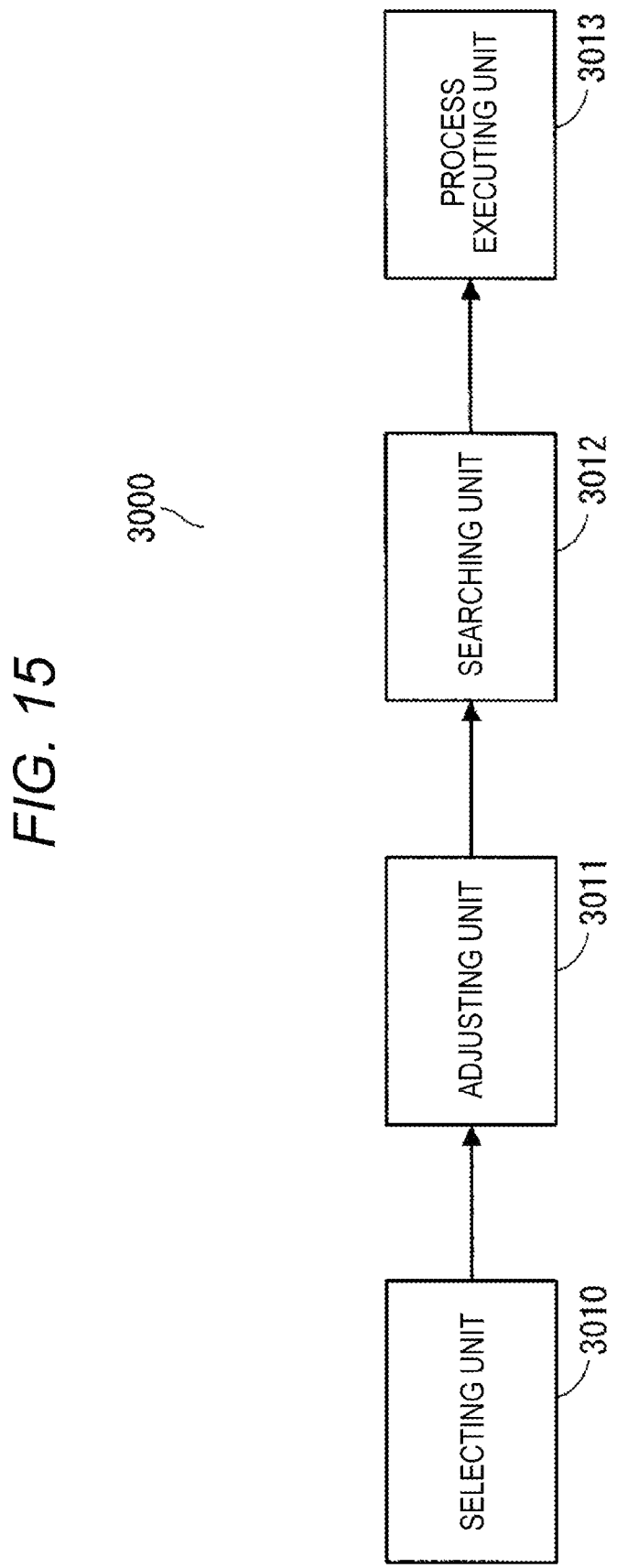
FIG. 15 is a block diagram of a processing unit of a third embodiment.
Figure 16:
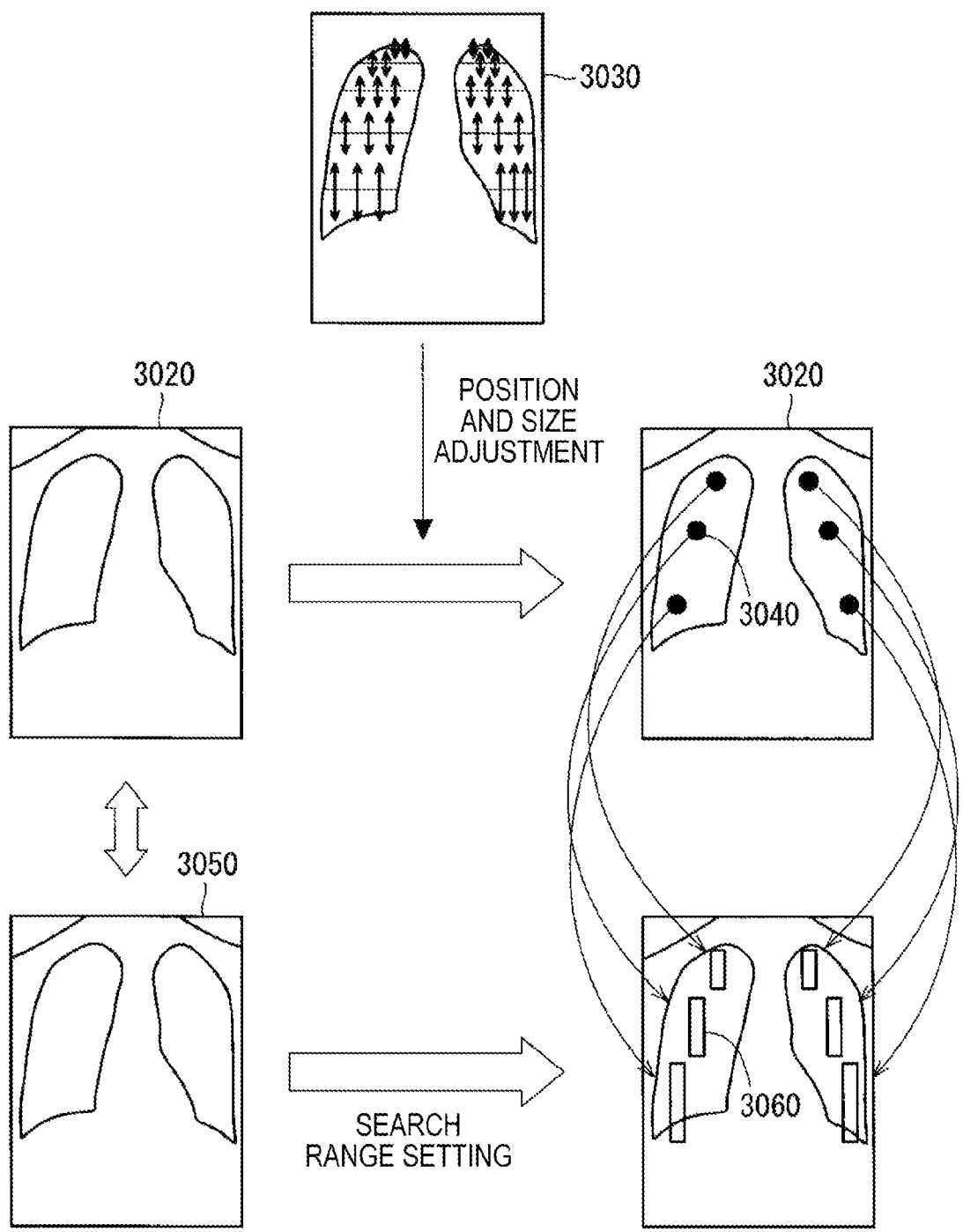
FIG. 16 is a schematic view showing an example of processing according to the third embodiment.

The block diagram in FIG. 15 shows the processing unit of the third embodiment. The schematic view in FIG. 16 shows an example of processing to be performed by the processing unit of the third embodiment. The example processing shown in FIG. 16 is to be performed in a case where lung field motion models representing lung field motion differences due to positions in the vertical direction are prepared for respective attributes.

The processing unit 3000 shown in FIG. 15 includes a selecting unit 3010, an adjusting unit 3011, a searching unit 3012, and a process executing unit 3013.

The selecting unit 3010 identifies the attribute of a medical video image, and selects the lung field motion model 3030 corresponding to the identified attribute from between two or more lung field motion model 1030 by referring to attribute information 1031, as in the second embodiment.

The adjusting unit 3011 adjusts the position and the size of the lung field motion model 3030 to a frame image 3020 sequentially selected from two or more frame images. As the position and the size of the lung field motion model 3030 are adjusted with respect to the two or more frame images, the position and the size of the lung field motion model 3030 are adjusted to the medical video image. As the position and the size are adjusted, the respective pixels constituting the frame image 3020 are associated with the lung field motions simulated by the lung field motion model 3030.

The searching unit 3012 searches the pixels constituting a frame image 3050 for the pixels corresponding to the respective pixels constituting the frame image 3020, the one frame image being the frame image 3020, the other frame image being the frame image 3050 generated after the frame image 3020 is generated.

In the search process, search ranges 3060 for the respective pixels 3040 constituting the frame image 3020 are set in the frame image 3050. The search ranges 3060 are set with the use of the lung field motions associated with the pixels 3040. Preferably, the orientations of the search ranges 3060 are adjusted to the directions of the lung field motions, the search ranges 3060 are made larger in the directions of the lung field motions as the lung field motions become larger, and as a result, the search ranges 3060 are made larger as the lung field motions become larger. The search ranges 3060 may be set in accordance only with the sizes of the lung field motions. For example, the orientations of the search ranges 3060 may be fixed, though the search ranges 3060 are made larger as the lung field motions become larger. The search ranges 3060 may be set in accordance only with the directions of the lung field motions. For example, the sizes of the search ranges 3060 may be fixed, though the orientations of the search ranges 3060 are adjusted to the directions of simulated lung field motions.

In a case where the orientations of the search ranges 3060 are adjusted to the directions of the lung field motions, the angles formed by the orientations of the search ranges 3060 and the directions of the lung field motions are within a predetermined range from 0 or 180 degrees, or preferably, 0 or 180 degrees.

Each of the search ranges 3060 has a rectangular shape, and the orientation of each of the search ranges 3060 is equal to the long-side direction thereof. The search ranges 3060 may not have rectangular shapes. For example, the search ranges 3060 may have elliptical shapes. In a case where each of the search ranges 3060 has an elliptical shape, the orientation of each of the search ranges 3060 is the long-axis direction thereof. More generally, the orientation of each of the search ranges 3060 is the longitudinal direction of the search range 3060. Alternatively, each of the search ranges 3060 may have a circular shape, a square shape, or the like.

Figure 17:
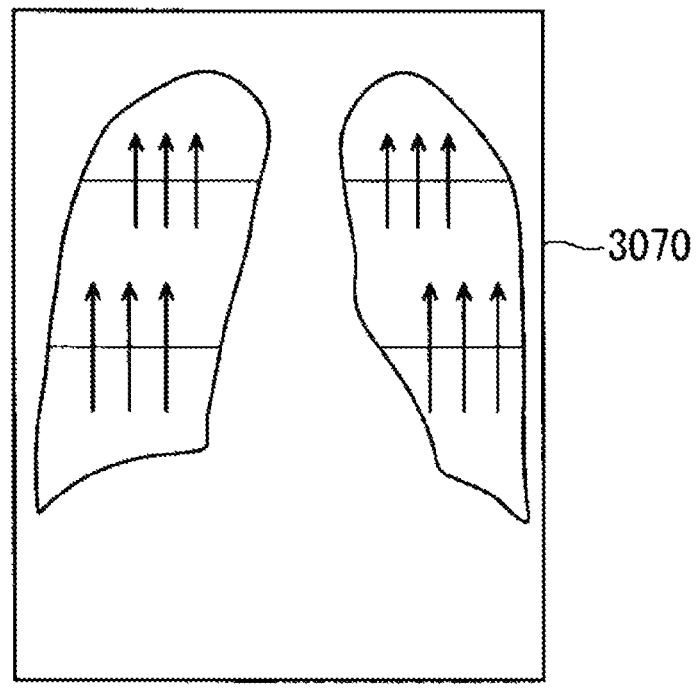
FIG. 17 is a schematic view of a lung field motion model.
Figure 18:
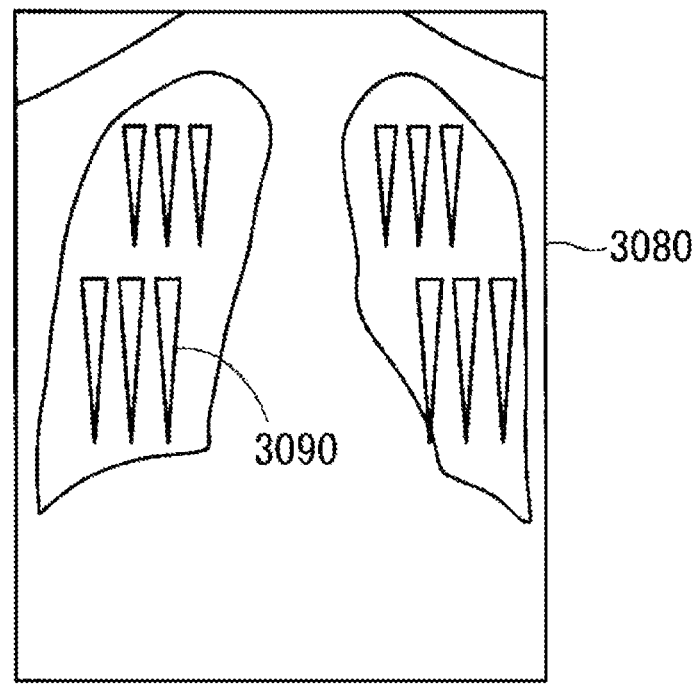
FIG. 18 is a schematic view of a frame image.

The schematic view in FIG. 17 shows a lung field motion model. The schematic view in FIG. 18 shows a frame image. The lung field motion model 3070 shown in FIG. 17 represents lung field motion differences due to positions in the vertical direction while the respiration phase is in an expiratory period.

In the frame image 3080 shown in FIG. 18, search ranges 3090 are set with the use of the lung field motion model 3070. In a case where the respiration phase is in an expiratory period, the orientations of the search ranges 3090 are adjusted to the upward direction, which is the direction of the lung field motions. Preferably, each of the search range 3090 becomes wider in an upward direction, which is the direction of the lung field motions.

In the search process, feature amounts are determined, and the search ranges are searched for pixels having high degrees of similarity in terms of the feature amounts. The feature amounts may be of any kind. For example, the feature amounts may be indicated by a density pattern. The search algorithm may be changed, or the usage of the lung field motion model in the search process may be changed.

The process executing unit 3013 generates a difference image between one frame image and the other frame image, the one frame image being the frame image 3020, the other frame image being the frame image 3050. In the generation of the difference image, the difference values as the pixel value differences between the respective pixels constituting the one frame image and the corresponding pixels are determined, and the difference values are set as the pixel values of the pixels constituting the difference image. The corresponding pixels have already been identified through the search conducted by the searching unit 3012. Alternatively, a difference image may be generated with the use of processing blocks as in the first embodiment.

The present invention has been described in detail, but the above described embodiments are examples in every aspect and do not limit the present invention. Therefore, it should be understood that numerous changes and modifications can be made to them without departing form the scope of the invention.

Although the present invention has been described and illustrated in detail, it is clearly understood that the same is by way of illustrated and example only and is not to be taken by way of limitation, the scope of the present invention being interpreted by terms of the appended claims.

What is claimed is:

1. An image processing device, comprising:
   a holding unit configured to hold a lung field motion model, the lung field motion model simulating lung field motion;
   an acquiring unit configured to acquire a medical video image by imaging of lungs after the lung field motion model is held by the holding unit, wherein when the medical video image is acquired the acquiring is performed by the acquiring unit independently of the lung field motion model; and
   a processing unit in communication with the holding unit and the acquiring unit, wherein the processing unit is configured to receive both the lung field motion model from the holding unit and the medical video image from the acquiring unit and wherein the processing unit is configured to process the medical video image received from the acquiring unit by using the lung field motion model received from the holding unit to generate a difference image.

2. The image processing device according to claim 1, wherein the processing unit comprises:
   a setting unit configured to set a processing block by using the lung field motion model, the processing block being a region for performing arithmetic processing on a frame image constituting the medical video image; and
   a process executing unit configured to process the medical video image by using the processing block.

3. The image processing device according to claim 2, wherein the setting unit makes the processing block larger, as the lung field motion in the lung field motion model becomes larger.

4. The image processing device according to claim 2, wherein the setting unit makes the processing block larger in the direction of the lung field motion, as the lung field motion in the lung field motion model becomes larger.

5. The image processing device according to claim 2, wherein the setting unit adjusts an orientation of the processing block to a direction of the lung field motion in the lung field motion model.

6. The image processing device according to claim 2, wherein
   the medical video image comprises a first frame image and a second frame image,
   the setting unit sets the processing block on each pixel constituting the first frame image, and
   the process executing unit generates a difference image between the first frame image and the second frame image by identifying pixels corresponding to respective pixels included in the processing block from among pixels constituting the second frame image, determining pixel value differences between the pixels included in the processing block and the pixels of the second frame image corresponding to the respective pixels included in the processing block, and setting a representative value of the pixel value differences as a difference value with respect to the pixels on which the processing block is set.

7. The image processing device according to claim 1, wherein the processing unit includes:
   a deforming unit configured to obtain a deformed medical video image by deforming the medical video image with the use of the lung field motion model; and
   a process executing unit configured to process the deformed medical video image.

8. The image processing device according to claim 7, wherein the deforming unit deforms the medical video image so that deformation becomes greater as the lung field motion in the lung field motion model becomes larger.

9. The image processing device according to claim 7, wherein
the medical video image includes a first frame image and a second frame image,
the deforming unit obtains a deformed first frame image by deforming the first frame image with the use of the lung field motion model, and obtains a deformed second frame image by deforming the second frame image with the use of the lung field motion, and
the process executing unit generates a difference image between the deformed first frame image and the deformed second frame image.

10. The image processing device according to claim 1, wherein
the medical video image includes a first frame image and a second frame image, and
the processing unit includes:
a searching unit configured to set a search range in the second frame image by using the lung field motion model, and search the search range for pixels of the second frame image corresponding to pixels constituting the first frame image, the search range being set for searching for the pixels of the second frame image corresponding to the pixels constituting the first frame image; and
a process executing unit configured to process the medical video image with the use of a result of the search conducted by the searching unit.

11. The image processing device according to claim 10, wherein the searching unit makes the search range larger, as the lung field motion in the lung field motion model becomes larger.

12. The image processing device according to claim 10, wherein the searching unit adjusts an orientation of the search range to a direction of the lung field motion in the lung field motion model.

13. The image processing device according to claim 10, wherein the searching unit makes the search range wider in a direction of the lung field motion in the lung field motion model.

14. The image processing device according to claim 10, wherein the process executing unit generates a difference image between the first frame image and the second frame image by identifying pixels corresponding to the respective pixels constituting the first frame image from among pixels included in the search range, and determining difference values between the respective pixels constituting the first frame image and the pixels of the second frame image corresponding to the respective pixels constituting the first frame image.

15. The image processing device according to claim 1, wherein
the medical video image comprises a frame image,
the holding unit holds two or more lung field motion models including the lung field motion model,
each of the two or more lung field motion models simulates lung field motion,
the holding unit further holds information capable of identifying respective respiration phases corresponding to the two or more lung field motion models, and
the processing unit comprises:
a selecting unit configured to obtain an identified respiration phase by identifying the respiration phase at the time when the frame image is generated, and select the lung field motion model corresponding to the identified respiration phase from between the two or more lung field motion models by referring to the information; and
a process executing unit configured to process the medical video image by processing the frame image with the use of the lung field motion model.

16. The image processing device according to claim 1, wherein
the holding unit holds two or more lung field motion models including the lung field motion model,
each of the two or more lung field motion models simulates lung field motion,
the holding unit further holds information capable of identifying respective attributes of the two or more lung field motion models, and
the processing unit comprises:
a selecting unit configured to obtain an identified attribute by identifying the attribute of the medical video image, and select the lung field motion model corresponding to the identified attribute from between the two or more lung field motion models by referring to the information; and
a process executing unit configured to process the medical video image by using the lung field motion model.

17. The image processing device according to claim 1, wherein the processing unit comprises:
an adjusting unit configured to obtain an adjusted lung field motion model by adjusting a position and a size of the lung field motion model to the medical video image; and
a process executing unit configured to process the medical video image by using the lung field motion simulated by the adjusted lung field motion model.

18. An imaging system, comprising:
an imaging device configured to image lungs and generate a medical video image; and
an image processing device comprising:
a holding unit configured to hold a lung field motion model, the lung field motion model simulating lung field motion;
an acquiring unit configured to acquire a medical video image by imaging of lungs after the lung field motion model is held by the holding unit, wherein when the medical video image is acquired the acquiring is performed by the acquiring unit independently of the lung field motion model; and
a processing unit in communication with the holding unit and the acquiring unit, wherein the processing unit is configured to receive both the lung field motion model from the holding unit and the medical video image from the acquiring unit and wherein the processing unit is configured to process the medical video image received from the acquiring unit by using the lung field motion model received from the holding unit to generate a difference image.

19. A non-transitory computer readable storage medium storing a computer program, which when executed by a computer, performs the following:
acquiring a medical video image obtained by imaging of lungs after a lung field motion model has been generated, wherein when the medical video image is acquired the acquiring is performed independently of the lung field motion model; and processing the medical video image by using lung field motion simulated by the lung field motion model to generate a difference image.

20. An image system, comprising:
a medical video image detector configured to generate a medical video image by imaging of lungs; and
a computer configured to:
  create a lung field motion model independently of the medical video image, the lung field motion model simulating lung field motion;
  hold the lung field motion model; and
  process the medical video image by using the lung field motion model to generate a difference image.

* * * * *